United States Patent [19]
Rele et al.

[11] Patent Number: 5,534,429
[45] Date of Patent: Jul. 9, 1996

[54] STRAIN OF CEPHALOSPORIUM HAVING ATCC ACCESSION NO. 74297, A PROCESS OF ISOLATING SAID STRAIN OF CEPHALOSPORIUM AND A PROCESS FOR PREPARING EXTRACELLULAR ENDOXYLANASE

[75] Inventors: Meenakshi V. Rele; Snehal M. Bansod; Mandayam C. Srinivasan, all of Pune, Ind.

[73] Assignee: Council of Scientific & Industrial Research, New Delhi, Ind.

[21] Appl. No.: 294,068

[22] Filed: Aug. 22, 1994

[51] Int. Cl.$^6$ .............................. C12N 9/24; C12N 9/26
[52] U.S. Cl. .................. 435/200; 435/201; 435/243; 435/255.1
[58] Field of Search .................... 435/200, 201, 435/255.1, 925

[56] References Cited

U.S. PATENT DOCUMENTS

| | | | |
|---|---|---|---|
| 5,116,746 | 5/1992 | Bernier et al. | 435/200 |
| 5,202,249 | 4/1993 | Kluepfel et al. | 435/201 |
| 5,407,827 | 4/1995 | Casimir-Schenkel et al. | 435/200 |

*Primary Examiner*—Herbert J. Lilling
*Attorney, Agent, or Firm*—Ladas & Parry

[57] ABSTRACT

Where is provided a process for preparing extracellular endoxylanase that is stable and active at high alkaline pH. The process includes growing a Ccphalosporium strain on xylan rich natural media supplemented with nitrogen-rich nutrients at high alkaline pH either by submerged or semi-solid fermentation. The Cephalosporium strain has been isolated from humus rich soil collected from Ganeshkind, Pune, India and growing at high alkaline pH in a range of from 5 to 10. The strain produces an extrcelluar-cellulase-free xylanase stable and active at high alkaline pH ranging from 5 to 10.

15 Claims, 2 Drawing Sheets

STRAIN OF CEPHALOSPORIUM HAVING ATCC ACCESSION NO. 74297, A PROCESS OF ISOLATING SAID STRAIN OF CEPHALOSPORIUM AND A PROCESS FOR PREPARING EXTRACELLULAR ENDOXYLANASE This invention relates to a new strain of Cephalosporium capable of growing at a pH in the range of 5–10, a process for the isolation of such novel strain and a process for the production of extracellular xylanase using the abovementioned strain. The xylanase prepared by the process described in the present invention exhibits good stability and activity under highly alkaline pH conditions.

BACKGROUND OF THE INVENTION

Xylan represents the major hemicellulose component in tropical plant biomass and world wide interest on microbial degradation of xylan has led to the discovery of several xylanases from a wide variety of microorganisms. The xylanase in all the instances studied are secreted in large quantities into the medium. In majority of cases the xylanases are also co-secreted with cellulase activity. The xylanases are by and large endoxylanases which result in the formation of xylo-oligomers leading to xylobiose as the predominant end product. The xylobiose is eventually hydrolyzed by B-xylosidase to yield the monomeric sugar xylose. Xylose finds extensive application as a source of the low calorie sweetener xylitol. The majority of the xylanases are co-secreted along with cellulasos and have their pH optima at or around neutral pH or even slightly acidic pH.

Recent interest on xylanases which are cellulase-free and stable at high alkaline pH has emanated from the realization that such xylanases could be extremely useful in the pulp and paper industries for biopulping, biobleaching and also in the manufacture of dissolving pulp. Besides being specific in their reactions at ambient temperatures, the use of xylanase also minimizes the use of toxic chemicals such as chlorine and chlorine dioxide which are environmentally hazardous (Viikari et al, In ACS Symp. Ser. 460: G. E. Leatham & E. M. Himmel (Eds.) American Chemical Society, Washington D.C.,1990). Strains producing alkaline xylanases are preferred to acidic xylanases for their use in the pulp and paper biotechnology. The search for cellulase-free alkali stable and active xylanases of microbial origin has resulted in the recent past in the discovery of several xylanases from bacteria, especially the genus Bacillus (Balkrishnan et.al. world J. Microbiol. Biotech. 8:626–31, 1992 Nakumura et. al. World J. of Mocrobiol. Biotech. 9:221–24, 1993) and actinomycetes (Vyas et. al. Biotech. Letters 12:225–228, 1990). Alkaline xylanases from bacteria are produced on either xylan or xylan-rich agricultural residues such as wheat bran at pH of 9.0 and above. These alkaline xylanases are active in the range of pH 7 to 9 and at temperatures between 50° and 60° C.

Fungi On the other hand are known to utilise biomass more efficiently and to secrete enzymes in larger quantities Fungal xylanases reported to date are active in the acidic range and are mostly co-secreted with cellulase.

SUMMARY OF THE INVENTION

The main objective of the present invention is therefore to identify fungi capable of growing at high pH values and secreting xylanases active at high pH. Identification of the species of the Cephalosporium capable of growing over a pH range of 5 to 10 and secreting a cellulase-free xylanase active over a pH range of 6 to 10 with maximum activity around pH 8 to 9 is the result of the sustained efforts by the inventors of the present invention.

DETAILED DESCRIPTION OF THE INVENTION

Figure 1:
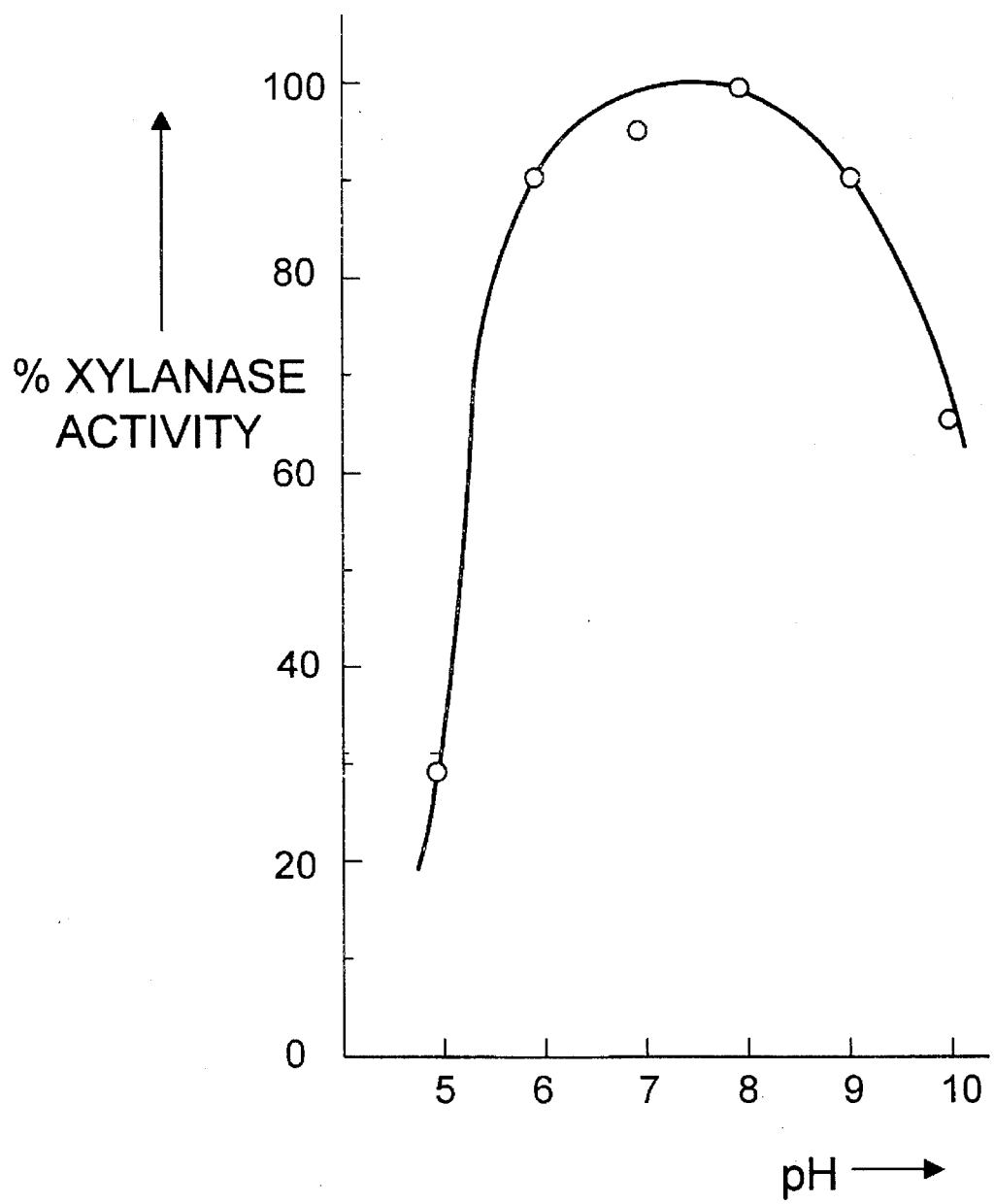
FIG. 1 is a graph showing of activity of the xylanase enzyme as a function of pH.

The novel alkalotolerant Cephalosporium strain is designated as NCL 87.11.9 which has been deposited at National Collection of Industrial Micro-organism (NCIM), at the Natienal Chemical Laboratory, Pune, India, (which is a recognized collection under the World Federation of Culture Collections.) under accession number 125] and also deposited in the American Type Culture Collection (ATCC), Rockville, Md., USA under their accession No. 74297. The fungal strain of Cephalosporium having the above accession numbers was isolated from humus-rich soil collected from Ganeshkind, Pune, India on a medium containing wheat bran and yeast extract adjusted to pH 9.5 to 10. The fungus was isolated in association with bacterial colonies but was successfully purified and confirmed to be capable of rapid growth and sporulation at high alkaline pH. Single spore colonies were then transferred into yeast extract, malt extract, xylan and agar (YMX) adjusted to pH 10 with sterile sodium carbonate and incubated at 28° to 30° C. A clear zone of hydrolysis around the growing colonies in the alkaline YMX medium was observed which gave the indication that the fungus was secreting the xylanase under the alkaline conditions of cultivation. The Cephalosporium strain grew rapidly producing abundant slimy sporeheads borne on short unbranched conidiophores arising out of aerial mycelium.

On the basis of the above growth characteristics as well as the morphology of the spores the fungus was identified as a species of the Cephalosporium which has been designated as mentioned above.

Xylanase production was studied in shake flask fermentations as well as in semisolid culture at 28° to 30° C. and under high alkaline pH. For submerged culture, the medium composition essentially included agricultural residues which are rich in xylan exemplified by wheat bran, rice bran, corn cobs, sugar cane bagasse or coconut fiber, either added as such or added after extraction with water after boiling as in the case of wheat bran and rice bran so that the major portion of the associated starchy material is removed. A nitrogen source for the fermentation is provided in the form of inorganic salts such as ammonium sulfate, sodium nitrate, ammonium nitrate or organic nitrogen supplement in the form of malt extract, yeast extract, corn steep liquor etc. In some of the fermentation media trace elements such as Iron, Zinc or, Manganese, were added in trace quantities but when agriculture residues were employed supplementation with trace metals was not observed to be essential.

Culture media for submerged culture were dispensed in Erlenmeyer flasks and supplemented with sterile sodium carbonate to raise the pH to 9.5 to 10. The vegetative inoculum was developed for 72–96 hrs, in a medium containing slightly lower concentrations of the carbon-nitrogen sources and generally 10–20 % (v/v) inoculum was transferred to the experimental flasks containing a higher concentration of the carbon nitrogen sources. The fermentation was carried out at 30° C. at 200–250 rpm for 3–4 days.

For semisolid culture either spore suspension from an agar slant (7–10 day old) or appropriate quantities of the vegetative inoculum as prepared for submerged culture was added to the autoclaved agricultural residue such as wheat bran or rice bran supplemented with appropriate nitrogen rich nutrients and mixed with requisite concentration of sodium carbonate to make the semisolid Koji highly alkaline. Incubation was carried out for 4–6 days after inoculation at the end of which the moldy KoJi was suitably diluted with water for extraction of the enzyme.

Figure 2:
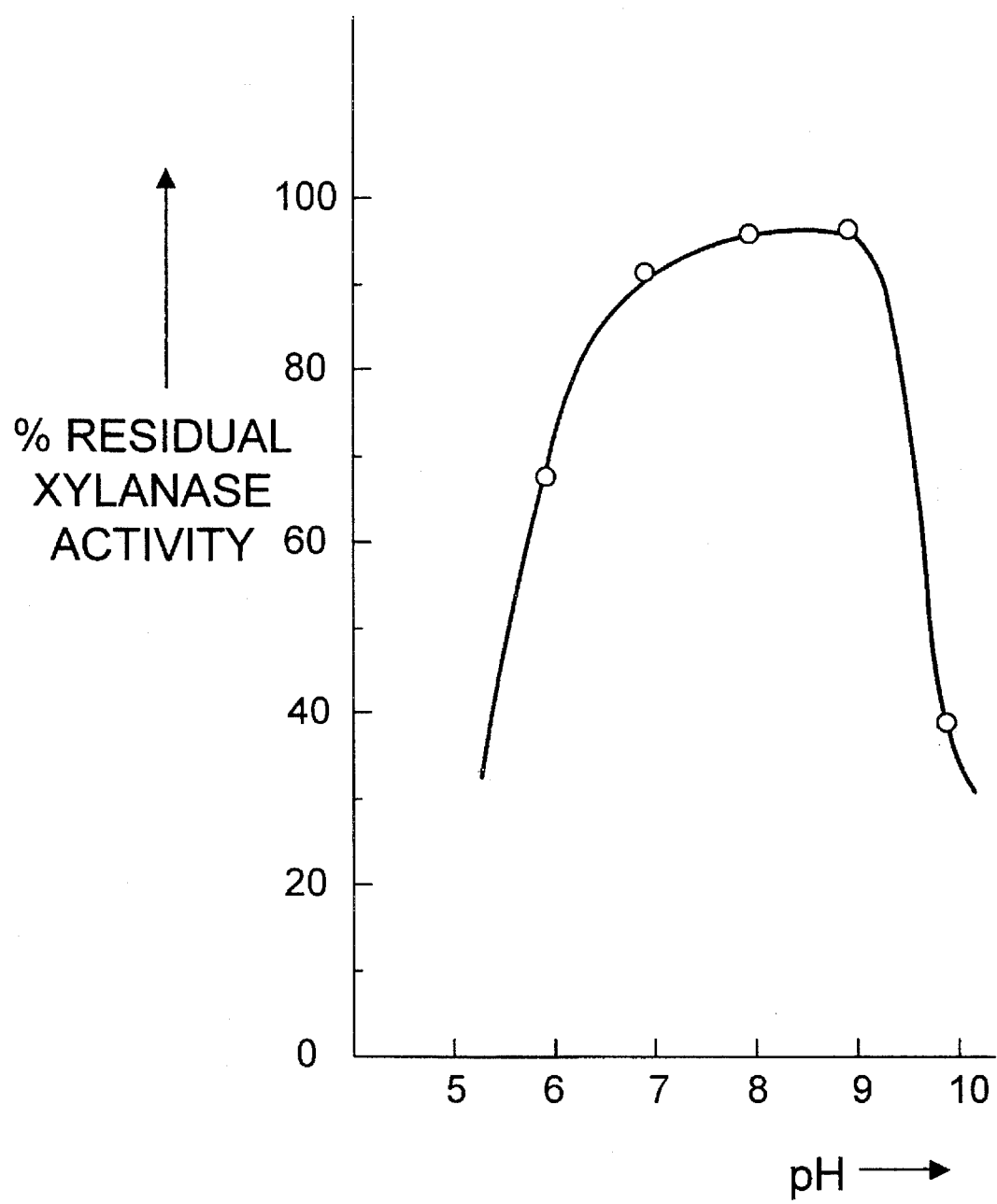
FIG. 2 is a graph showing the influence of pH on stability of the enzyme.

The levels of associated cellulase activity in the culture filtrates in either type of fermentation were negligible or totally absent. Xylanase assay was carried out using standard Dinitro salicylic acid procedure as described by Balkrishnan et. al. 1992 using oatspelt xylan as the substrate. The determination of optimum pH and stability of the xylanase enzyme produced by the process of the present invention was done as follows:

a) For determination of optimum pH the enzyme was (1:50) diluted in 0.1M Citrate phosphate buffer (pH 5 and 6), 0.1M phosphate buffer (pH 7 and 8), 0.1M Glycine-NaOH buffer (pH 9 and 10) and assayed in the respective buffer for 30 minutes at 40° C. The results of the experiment have been illustrated in FIG. 1 accompanying and forming the part of this specification. It is observed that the enzyme is active between pH 6 and 10.

b) The influence of pH on stability of the enzyme was studied as follows :

The enzyme was diluted (1:50) in 0.1M Citrate phosphate buffer (pH 5 and 6), 0.1M phosphate buffer (pH 7 and 8), 0.1M Glycine-NaOH buffer (pH 9 and 10) and incubated for 15, minutes at 40° C. The activity of the enzyme after incubation was assayed using the Dinitro Salicylic acid method as mentioned earlier. The results are illustrated in FIG. 2 wherein it is observed that the enzyme is stable in the range of pH 6 to 9, with maximum stability at pH 9.

Gel filtration studies of the crude culture filtrates of the enzymes indicated presence of two xylanases having different molecular weights of 70,000 and 28,000 with 90% of the activity being exhibited by the latter. The lower molecular weight enzyme has been subjected to extensive purification studies leading to homogeneity on native and sodium dodecyl sulphate polyacrylamide gel electrophoresis. The properties of the homogeneous xylanase enzyme was similar to the crude enzyme in the culture filtrate with regard to the novel properties described herein.

The invention is described herein with examples to illustrate a representative picture of the conditions leading to the production of extracellular xylanase using the Cephalosporium and isolation of the major xylanase, which should not be construed to limit the scope of the invention in any manner whatsoever.

EXAMPLE 1

The example illustrates the isolation of the Cephalosporium fungal strain. This experiment was carried out by plating the soil suspension in water, the soil collected from a site at Ganeshkhind, Pune, india, on a medium comprised of 3% wheat bran extracted free of starch (by autoclaving at a pressure of 15 psi for 20 minutes) supplemented with 1% yeast extract and 2% agar adjusted to pH 10 by sterile addition of 10% sodium carbonate solution separately sterilized, the final concentration of alkali being 1%. Incubation was carried out at 28° to 30° C. and the fungal colony which developed after 7 to 10 days was purified through single spore culture and subcultured on 1% Yeast extract, malt extract and xylan, adjusted to alkaline pH by aseptic addition of 10% sodium carbonate to a final concentration of 1%. Clearance of the xylan by the growing colonies on the above medium gave positive evidence of extracellular xylanse secretion under highly alkaline pH conditions by the fungal strain.

EXAMPLE 2

Fermentation using the strain Cephalosporium N.C.L. 87-11-9 was carried out in shake flasks in a medium containing (grams per liter) Wheat bran, 50; Yeast extract, 10. The pH of medium was raised to 10 by addition of 10% of sodium carbonate separately autoclaved. Spore suspension from a 7 day old slant was used for preparing the seed culture, the composition of which is 3% wheat bran, yeast extract 1% and sodium carbonate 1%. This was incubated on a rotary shaker for 72 hours at a temperature of 28° C. and was used to initiate the shake flask experiments. The shake flask experiment was run for 96 h at 28° C. on a rotary shaker (200 rpm) after which it was harvested by centrifugation at 10,000 rpm for 30 min. The supernatant was taken and assayed for xylanase activity and 12–16 IU/ml, (240 IU/g of wheat bran) of the activity was obtained.

EXAMPLE 3

Purification of the Xylanase: The culture filtrate [500 ml] was brought to 90 % saturation by the addition of 300 g ammonium sulphate. The precipitate was centrifuged at 10,000 rpm for 30 min, dissolved in a minimum amount [55 ml] of 10 mM potassium phosphate buffer [pH 7] and then dialyzed extensively with the same buffer. The dialyzed enzyme was then treated with 0.4 % polyethylenimine [adjusted to pH 8 with 1N HCl] for 30 min. The supernatant was collected and passed through a CM- Cellulose column [1.5×20 cm] pre-equilibrated with 10 Potassium Phosphate buffer [pH 7]. The unadsorbed fractions showing xylanase activity were pooled and concentrated. The protein was then adsorbed at the rate of 12 ml/h onto a DEAE Sephacel column [1.5–18 cm]. The elution of the bound enzyme was affected with a linear gradient [120 ml total volume] of potassium chloride [0–1M] in 10 mM phosphate buffer pH 7,0. Fractions containing Xylanase activity were pooled and concentrated to 5 ml using an Amicon stirred cell. This preparation was homogeneous when analysed on native and SDS-PAGE gels. The yield of the purified xylanase ranged from 35 to 40%.

EXAMPLE 4

Semisolid fermentation was carried out in 500 ml flasks in a medium containing wheat bran, 10 gm; Yeast extract, 0.8 gm; mixed with 8 ml water and pH raised to above 9 by addition of 20% sodium carbonate. Spore suspension from a 7 day old slant was used for preparing the seed culture the composition of which is 3% wheat bran, yeast extract 1% and sodium carbonate 1%. This was incubated on a rotary shaker for 72 hours at a temperature of 28° C. and was used to initiate the fermentation.

The semisolid moldy Koji was diluted with distilled water after 144 hrs, for extraction of the enzyme. The flask containing the semisolid Koji was taken and distilled water (50 ml) added and kept on a shaker at 150 rpm for 1 h, the enzyme was obtained on centrifugation for 20 min at 10,000 rpm, this was repeated thrice. The enzyme obtained was assayed and activity ranging from 50–60 IU/ml or 800–820 IU/gm of wheat bran was obtained in 144 hrs.

We claim:

1. A process for preparing extracellular endoxylanase that is stable and active at high alkaline pH comprising growing Cephalosporium strain deposited at American Type Culture Collection bearing accession number 74297 on xylan rich natural media supplemented with nitrogen-rich nutrients at high alkaline pH either by submerged or semisolid fermentation, said Cephalosporium strain having been isolated from humus rich soil collected from Ganeshkind, Pune, India and growing at high alkaline pH in a range of from 5 to 10 and said strain producing an extracellular-cellulase-free xylanase stable and active at high alkaline pH ranging from 5 to 10.

2. A process as claimed in claim 1 wherein the source of xylan in the fermentation medium is selected from purified xylan or xylan-rich residues.

3. A process as claimed in claim 2 wherein the xylan-rich residues are selected from wheat bran, corn cob, bagasse or coconut pith.

4. A process as claimed in claim 1 wherein the nitrogen rich nutrients for the growth of the Cephalosporium are inorganic or organic nitrogenous materials.

5. A process according to claim 4 wherein the nitrogenous materials are selected from ammonium sulphate, ammonium nitrate, yeast extract, malt extract or corn steep liquor.

6. A process as claimed in claim 1 wherein the pH of the medium is adjusted in the range of 5 to 10 by addition of sterile alkali to a final concentration of 1 to 3%.

7. A process according to claim 6 wherein the alkali is selected from sodium carbonate, sodium hydroxide, or potassium carbonate.

8. A process as claimed in claim 1 wherein the submerged or semisolid fermentation is carried out at temperatures between 20°–30° C.

9. A process according to claim 8 wherein the fermentation is carried out at temperatures of 28°–30° C.

10. A process as claimed in claim 1 wherein separation of the xylanase is effected by salting out method, adsorption on and elution from ion exchange columns or ultrafiltration.

11. A process as claimed in claim 1 wherein the mixture of xylanase is purified with inorganic salts.

12. A process according to claim 11 wherein the inorganic salts are selected from ammonium sulphate, sodium chloride or magnesium chloride.

13. A process according to claim 1 wherein the mixture of xylanase is purified with organic compounds.

14. A process according to claim 12 wherein the organic compounds are selected from polyethylenimine, protamine sulphate or streptomycin sulphate.

15. A process as claimed in claim 10 wherein the ion exchangers used in the ion exchange column for the separation of xylanase are selected from the group consisting of carboxymethyl cellulose, dieethyl amino ethyl cellulose, diethyl amino ethyl Sephacel and cellulose phosphate.

* * * * *